United States Patent [19]

Cordes, III et al.

[11] 3,970,639
[45] July 20, 1976

[54] ETHYL α-CYANO β-(N-METHYL-N-CYCLOHEXYLAMINO) ACRYLATE STABILIZER

[75] Inventors: William F. Cordes, III, East Brunswick; Robert E. Diehl, Trenton, both of N.J.

[73] Assignee: American Cyanamid Company, Stamford, Conn.

[22] Filed: Sept. 22, 1975

[21] Appl. No.: 615,871

[52] U.S. Cl. ............... 260/45.85 A; 260/465 D
[51] Int. Cl.² ............... C08J 3/20; C07C 121/00
[58] Field of Search ............... 260/465 D, 45.85 A, 260/45.85 N

[56] References Cited

UNITED STATES PATENTS

| | | | |
|---|---|---|---|
| 2,850,521 | 9/1958 | Mower | 260/465 D |
| 3,079,366 | 2/1963 | Boyle et al. | 260/45.85 A |
| 3,462,475 | 8/1969 | Strobel et al. | 260/45.85 A |

OTHER PUBLICATIONS

Index Chemicus, 21, 63462 (1966).

*Primary Examiner*—V.P. Hoke
*Attorney, Agent, or Firm*—Philip Mintz

[57] ABSTRACT

Polycarbonate is effectively stabilized against degradation by ultraviolet radiation by ethyl α-cyano-β-(N-methyl-N-cyclohexylamino)acrylate.

3 Claims, No Drawings

ETHYL α-CYANO-(N-METHYL-N-CYCLOHEXYLAMINO) ACRYLATE STABILIZER

This invention relates to a novel compound and to its use to stabilize polycarbonates against degradation on exposure to ultraviolet radiation.

Polycarbonates can be formed into useful articles, such as pipe, hollow objects (e.g. bottles, tumblers, etc.), film, sheet, lenses, hard hats, etc. by such process as injection molding, extrusion, blow-molding, etc. Because of their desirable properties and ease of forming into useful articles, polycarbonates have attained wide commercial utilization. In some of these uses, the polycarbonate is exposed to ultraviolet radiation, such as in sunlight. As is well known, such exposure causes degradation of the polycarbonate, leading to discoloration and embrittlement. It is an object of this invention of provide a novel compound useful, when incorporated in polycarbonates, for inhibiting degradation caused by ultraviolet radiation.

In accordance with the present invention, it has been found that ethyl α-cyano-β-(N-methyl-N-cyclohexylamino)-acrylate having the formula:

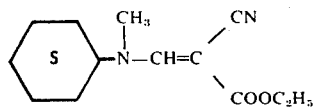

is effective for inhibiting degradation of polycarbonate on exposure to ultraviolet radiation.

This compound may be incorporated into polycarbonate by any of the standard techniques, including milling, screw extruding, Banbury mixing, swelling, etc. This compound is effective over a wide concentration range of about 0.1 to about 5.0 percent based on weight of polycarbonate. Preferably, it is used at a concentration of about 0.5 to about 2.0 percent on weight of polycarbonate. Other additives, such as dyes, foaming agents, pigments, plasticizers, thermal stabilizers, etc. may also be added to the polycarbonate for their usual functions.

This invention is further illustrated in the following examples, wherein all parts are by weight unless otherwise stated.

EXAMPLE 1

A mixture of 7.21 grams (0.064 mole) of N-methyl-N-cyclohexylamine and 10.3 grams (0.07 mole) of triethyl orthoformate was heated to 105°C. and 6.9 grams (0.06 mole) of ethyl cyanoacetate was slowly added thereto. The temperature gradually rose until ethanol began to distill over. After 11.4 milliliters of distillate was collected, the reaction mixture was cooled to room temperature and poured into water. The aqueous mixture was extracted with diethyl ether, dried over anhydrous magnesium sulfate, and evaporated to obtain 14.0 grams of a dark oil. The oil was heated under vacuum to remove some distillable material and the remainder was extracted with three portions of hot cyclohexane which, on cooling, gave a total of 5.7 grams of light tan powder. The powder was recrystallized from cyclohexane, yielding 4.0 grams melting at 65°–70°C. Further recrystallization from petroleum ether gave ethyl α-cyano-β-(N-methyl-N-cyclohexylamino)acrylate as fine white plates, melting point 71°–72°C.

Analysis: Calculated for $C_{13}H_{20}N_2O_2$: C, 66.07; H, 8.53; N, 11.86 Found: C, 65.98; H, 8.54; N, 11.72.

EXAMPLE 2

A test film was prepared by adding the stabilizer, ethyl α-cyano-β-(N-methyl-N-cyclohexylamino)acrylate, to a ten percent solution of water-free unstabilized polycarbonate in chloroform, casting, and drying at 2°–25°C. to obtain a film one mil thick. The quantity of stabilizer added was one percent on weight of polycarbonate. The film was exposed to ultraviolet light in an Atlas Xenon Weather-Ometer (no water spray in the Weather-Ometer) until it became embrittled to the point of complete destruction. The efficiency of the stabilizer in preventing degradation is measured in terms of the time in hours to failure of the film over a control sample which contains no stabilizer. This film showed an increase of 2500 hours to failure (a 166% increase) compared to a control film without stabilizer.

We claim:
1. Polycarbonate stabilized against the deteriorating effects of ultraviolet radiation by an effective amount of a stabilizer which is ethyl α-cyano-β-(N-methyl-N-cyclohexylamino)acrylate.
2. A composition as defined in claim 1 wherein said stabilizer is present in an amount of 0.1 to 5.0 percent on weight of polycarbonate.
3. α-Cyano-β-(N-methyl-N-cyclohexylamino)acrylate.

* * * * *